United States Patent [19]

Knopp et al.

[11] 4,203,221
[45] May 20, 1980

[54] GAS-DRIVEN HANDPIECE HAVING VIBRATION ISOLATING MEANS

[75] Inventors: Arthur A. Knopp, Chalfont; John E. Nash, Downington; Richard P. Lewis, Springfield, all of Pa.

[73] Assignee: Syntex (U.S.A.) Inc., Palo Alto, Calif.

[21] Appl. No.: 947,214

[22] Filed: Sep. 29, 1978

[51] Int. Cl.² ............................................... A61C 1/10
[52] U.S. Cl. ..................................................... 433/117
[58] Field of Search ........................................ 32/27, 26

[56] References Cited

U.S. PATENT DOCUMENTS

| | | | |
|---|---|---|---|
| 2,202,299 | 5/1940 | Pelkey | 32/27 |
| 3,499,223 | 3/1970 | Lieb et al. | 32/27 |
| 3,936,940 | 2/1976 | Loge | 32/26 |

FOREIGN PATENT DOCUMENTS

| | | | |
|---|---|---|---|
| 1255856 | 12/1967 | Fed. Rep. of Germany | 32/27 |
| 2354082 | 2/1978 | France | 32/27 |

Primary Examiner—Louis G. Mancene
Assistant Examiner—John J. Wilson
Attorney, Agent, or Firm—John A. Dhuey; Joseph I. Hirsch

[57] ABSTRACT

A dental handpiece is disclosed having at least two connectable portions and having a substantially rigid connection between the two connectable portions, there being resilient means forming a portion of the substantially rigid connection. The resilient means inhibits transfer of vibration from one of the connectable portions which contains a gas-driven motor to the other connectable portion which provides a hand-grippable surface.

18 Claims, 8 Drawing Figures

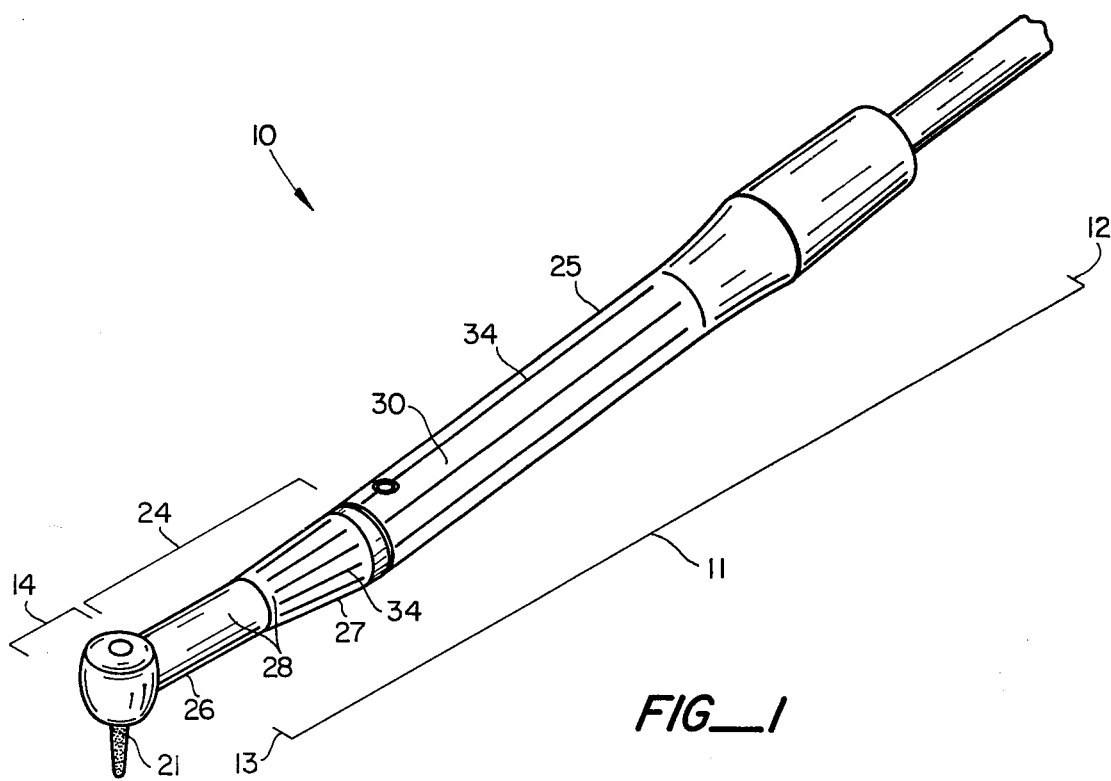
FIG__1
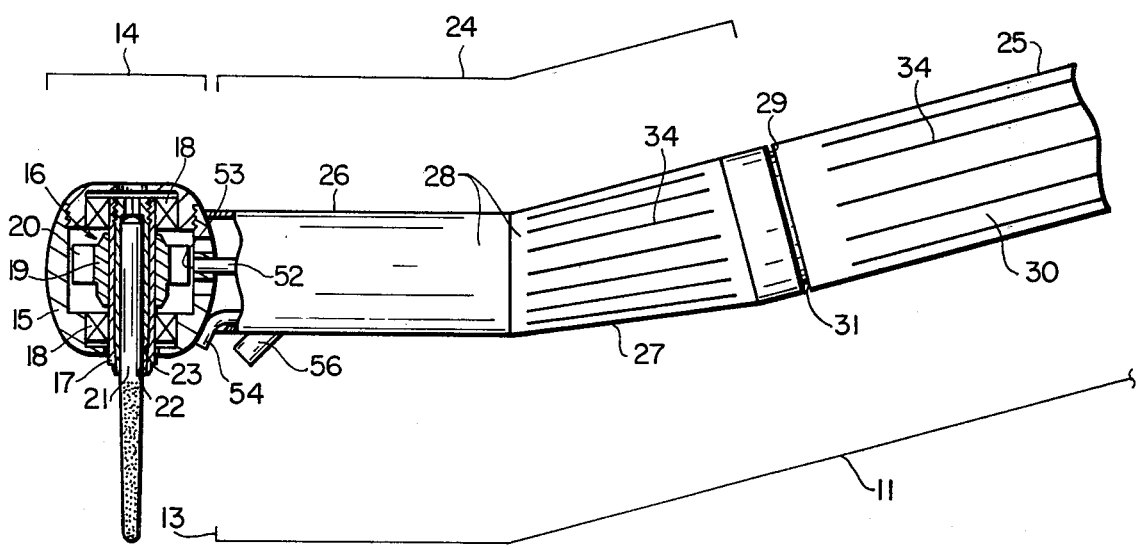
FIG__2

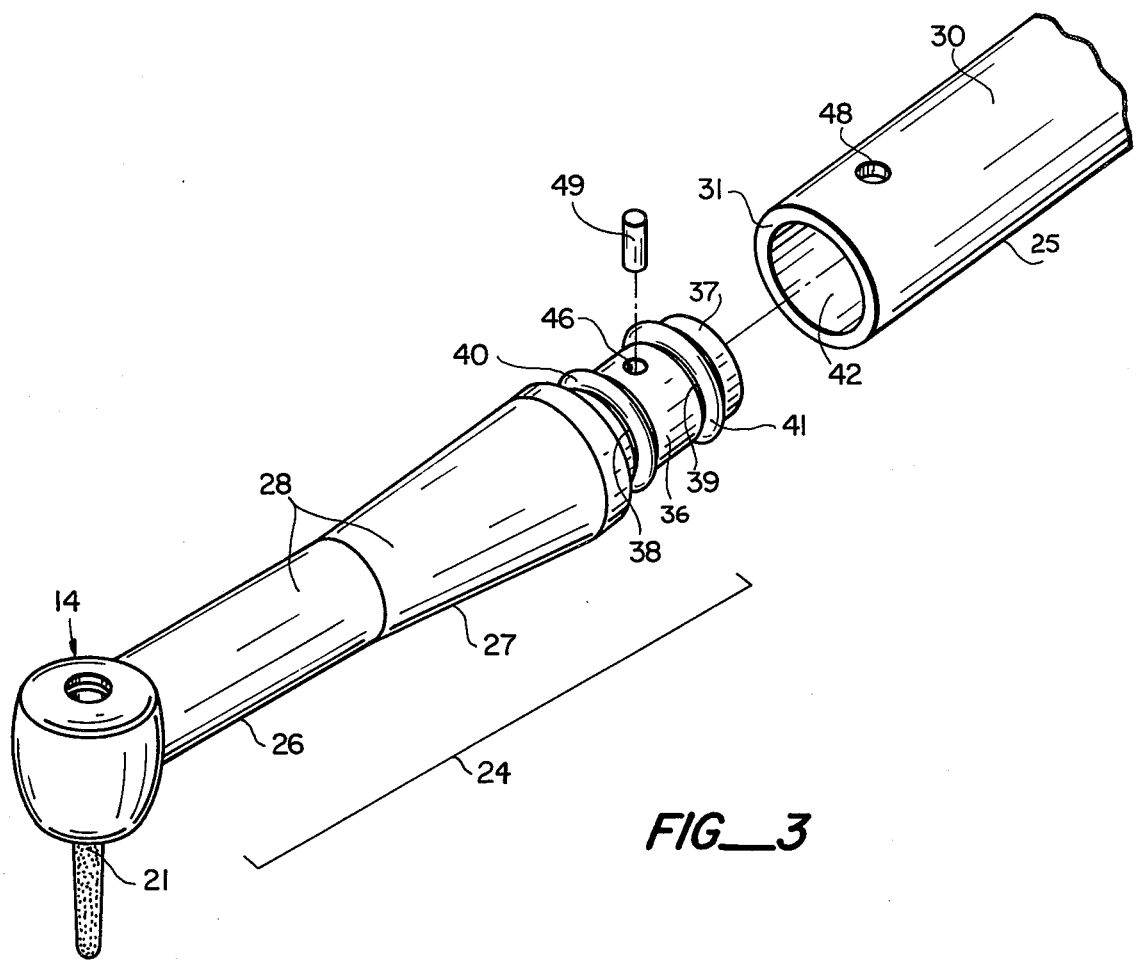
FIG_3
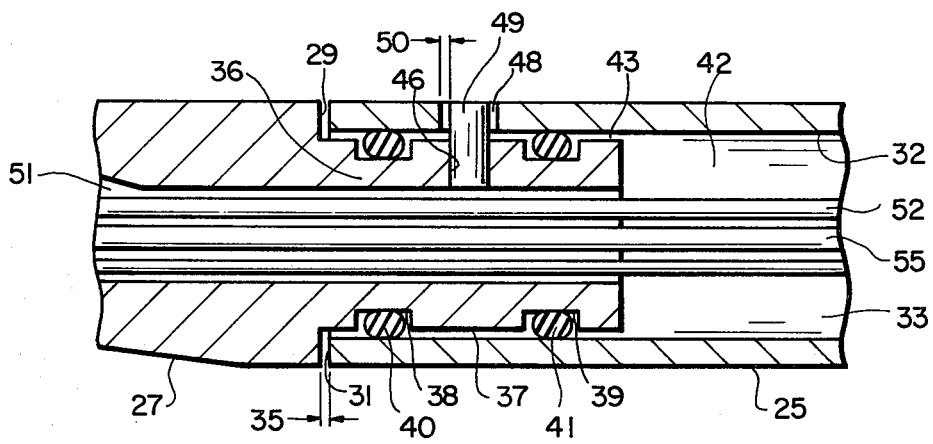
FIG_4

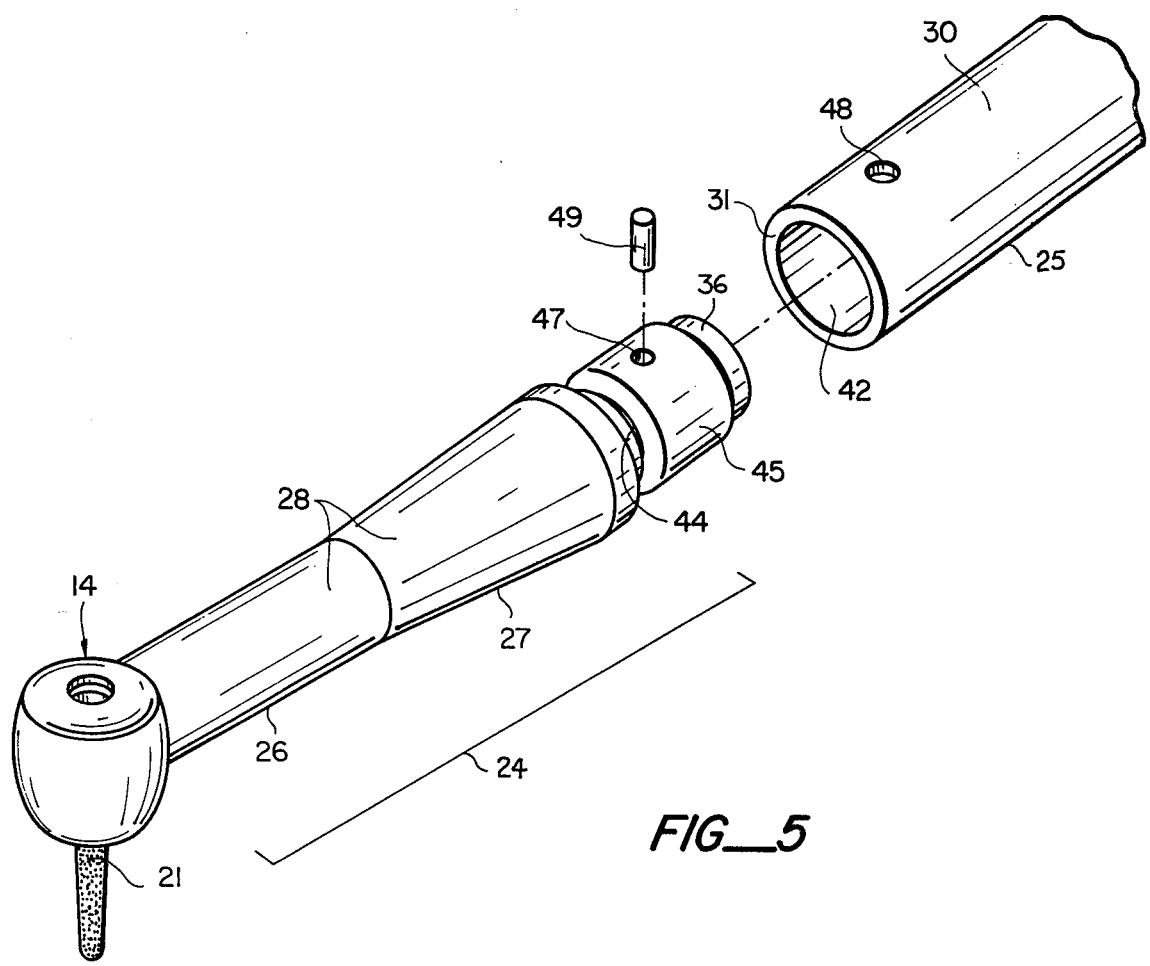
FIG_5
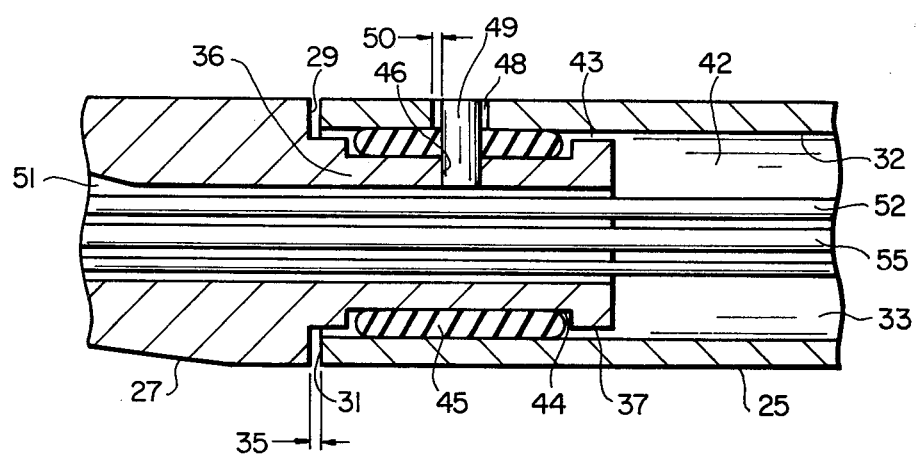
FIG_6

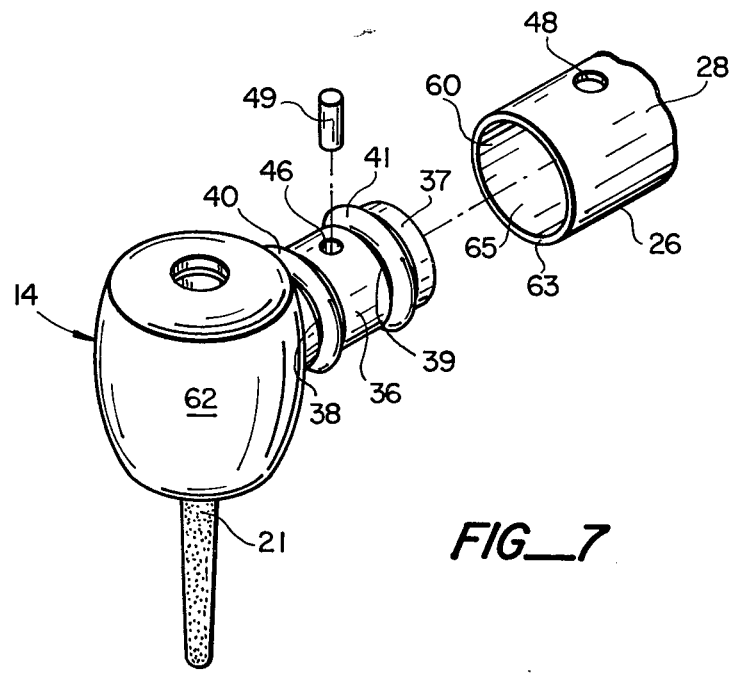
FIG_7
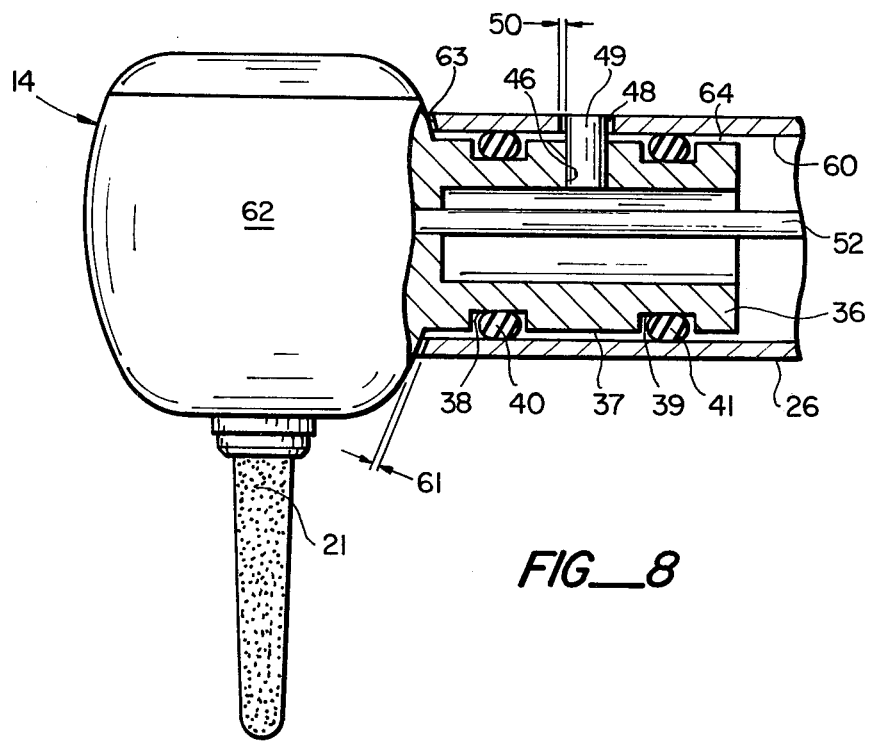
FIG_8

GAS-DRIVEN HANDPIECE HAVING VIBRATION ISOLATING MEANS

BACKGROUND OF THE INVENTION

1. Field of the Invention

Dental handpieces having gas-driven motors are well known. Of particular interest herein is a high-speed gas-driven dental handpiece having decreased noise and improved vibration damping characteristics.

2. State of the Art

During use of a high-speed gas-driven dental handpiece, rotor speeds are attained of 250,000 to 400,000 r.p.m. or more. While these high speed motors provide increased working efficiency as compared to lower speed motors for many dental applications, the substantially increased amounts of noise or vibration, or both, generated by the high speed motor can be quite disturbing to dentist and patient alike. Also, at certain critical rotor operating speeds, resonance effects between the motor and other portions of the dental handpiece may substantially intensify or amplify the noise or vibration originating from the gas driven motor.

It is a requirement of a dental handpiece that the handle portion provide a user with good tactile control over the instrument to ensure safe and efficient dental work within a patient's mouth. One aspect of good tactile control is provided by a handle portion having sufficient rigidity to ensure positive and direct transmittal of forces from the user's hand to the work site within the patient's mouth. It is a problem, however, that with currently available dental handpieces having rigid handle portions, vibration is readily transmitted from the motor housing of the handpiece to the hand-grippable portion of the handle.

Several attempts have been made to reduce the noise or vibration that may originate from a high-speed gas-driven motor. For example, in U.S. Pat. No. 3,499,223 to Lieb et al there is disclosed a high speed dental handpiece having vibration damping rings fabricated of non-metallic, rubbery materials interposed between the metallic rotor bearings and a metallic motor housing. These vibration damping rings tend to inhibit transfer of vibration from the rotating elements of a high speed motor to its housing. Further improvements in the arrangement of vibration damping elements upon a turbine cartridge assembly of a high-speed gas-driven motor are disclosed in U.S. application Ser. No. 947,215 of F. W. Kerfoot, Jr., filed on Sept. 29, 1978, the disclosure of which is incorporated herein by reference.

Though the interposition of vibration damping elements between a turbine rotor assembly and a motor housing tends to inhibit transfer of vibration or noise, total isolation of the rotating elements from the non-rotating elements of a handpiece is difficult to attain inasmuch as some rigid connection between the rotor and the housing is necessary for proper rotor alignment or for static preloading of rotor bearings within the housing. Hence, there remains a problem of transfer of vibration from the rotor to the motor housing and the consequent problem of resonance-effects enhancement at certain critical speeds between the gas-driven motor and other portions of the dental handpiece, such as the hand-grippable portion.

There is need, therefore, for a high-speed dental handpiece in which a gas-driven motor is substantially completely isolated from a handle portion with respect to transfer of vibration, so that the transfer of vibration from the gas-driven motor to the handle portion and the consequent generation of noise may be minimized during use of the dental handpiece, without significant decreases in user tactile control over the handpiece.

SUMMARY OF THE INVENTION

A dental handpiece according to the present invention having a handle portion which is substantially isolated from the gas-driven motor, as to transfer of vibration from the motor to other portions of the handpiece, is provided by a handle portion having a proximal end and a distal end, a housing for a gas-driven motor connected to the handle portion at its distal end, the handle portion including a first handle member having an outer wall and an end wall and a second handle member having an outer wall and an end wall, the first and second handle members connectable to each other at a junction so as to form a substantially continuous elongated handle portion with the outer wall portions providing a surface for gripping the handpiece, and means for forming a substantially rigid connection between the first handle member and the second handle member adjacent the junction when the first and second handle members are in proximate abutting relationship, the means for forming the substantially rigid connection including resilient means interposed between the first and the second handle members, the resilient means having a vibration-transmitting property of a character that substantially inhibits transfer of vibration between the first and second handle members. The one or more resilient means are so positioned as to be between and in contact with both of the handle members, yet prevent direct contact therebetween. This separation of the two handle members helps to reduce the direct transfer of vibrations between the two handle members.

It is a feature of a dental handpiece of the present invention that although the substantially rigid connection contains resilient, vibration-absorbing means, there is substantially no decrease in the integrity of the rigid connection between the two handle members. Thus a handpiece operator may experience a low level of vibration while at the same time have good tactile control in manipulating the handpiece during its use. This feature is more specifically attained wherein the means for forming the rigid connection between the first and second handle members comprises an elongated boss member projecting from one of the first and second handle member end walls, the boss member having at least one side wall, the other of the first and second handle members having a chamber in the end wall thereof which chamber has, or is defined by, at least one inner side wall of the other of the first and second handle members, the elongated boss member and the chamber each having a configuration complementary to the other so that a mating relationship is formed when the handle member end walls are in proximate abutting relationship. The elongated boss member has a diameter less than the diameter of the chamber such that when the elongated boss member and the chamber are in mating relationship the difference in diameters provides a gap between adjacent portions of the side wall of the elongated boss member and the side wall of the chamber. The resilient means interposed between the first and second handle members comprises in one embodiment, a continuous band of resilient material overlying the elongated boss member, the band of material having a thickness sufficient to provide an initial compression of the band of material between the boss member side wall and the chamber side wall when the elongated boss member and the chamber are in mating relationship. In another embodiment, two (or more) resilient elements of an appropriate material are positioned between adjacent portions of the side walls of the two handle members. Thus, for example, two (or more) O-rings can be secured at spaced positions on the side wall of the elongated boss member to dampen the transmission of vibration between the two handle members while holding the two handle members apart within a connection that is sufficiently rigid to provide the tactile control required during use of the handpiece.

The elongated boss member can be a cylindrically shaped shaft projecting from one of the first and second handle member end walls. The chamber will thus be cylindrically shaped and have longitudinal and radial dimensions slightly greater than those of the cylindrically shaped shaft, with the resilient means comprising one or more annular shaped elements circumferentially overlying the shaft. The resilient means may comprise a continuous band of material overlying a sufficient portion of the side wall of the shaft to prevent the two handle members from directly contacting each other during handpiece use. Alternatively, the resilient means may comprise at least two O-rings in spaced relationship along the axis of the shaft. With either construction, metal-to-metal contact between the metallic handle members is substantially prevented by the presence of the resilient means therebetween. Contact between the abutting end walls of the handle members is prevented by the maintenance of a gap between the adjacent end walls of the handle members. Generally, the gap has a dimension in the range of about 0.002 inch to about 0.015 inch, the range preferably being about 0.007 inch to about 0.010 inch.

In order to maintain the handle member end walls in proximate abutting relationship when the shaft is in mating relationship with the chamber, there can be further provided means for preventing axial and rotational movement of the handle members relative to one another after the handle members have been brought together and the axial movement-preventing means appropriately employed. For example, the shaft can be provided with a relatively small recess and the overlying handle member can have a relatively small opening or port extending through the side wall thereof. The recess and port are brought into alignment when the two handles members are in proximate a butting relationship. A stop pin positioned within the opening and extending into the recess prevents axial and rotational movement of the handle members relative to each other. The stop pin preferably has a sleeve fit within the recess in the shaft, there being a clearance fit between the stop pin and the opening in the handle member having the chamber. Alternatively, the stop pin may have a sleeve fit within the opening in the wall of the handle member which has the chamber, there being a clearance fit provided between the stop pin and the walls of the recess in the shaft.

It is preferred, in those embodiments having a stop pin as a part of the substantially rigid connection, that the stop pin have a diameter less than 15 percent of the diameter of the handle member shaft.

As another aspect of the invention, a dental handpiece may have a substantially rigid, vibration transmission-inhibiting connection between other connectable portions of the handpiece. For example, the dental handpiece may comprise a handle portion having a proximal end and a distal end, a head portion having a housing for a gas-driven motor, the head portion connected to the handle portion at the distal end, means for forming a substantially rigid connection between the head portion and the handle member distal end, the means for forming the substantially rigid connection including resilient means interposed between the head portion and the handle portion distal end, so that the head portion and the handle portion are not in direct contact with each other, the resilient means substantially inhibiting the transfer of vibration between the head portion and the handle portion during use of the dental handpiece.

In this embodiment of the invention, the substantially rigid connection between the handle portion and the head portion may comprise elongated boss member and chamber elements with resilient means interposed between adjacent side walls thereof, as described above for the substantially rigid connection between the first and second handle members.

It should be understood that the term "substantially rigid connection" as used with respect to embodiments of the present invention is intended to designate a connection between connectable portions of the handpiece that is sufficiently rigid to provide good tactile control over a handpiece for all the usual manipulative applications encountered by a dental handpiece user.

DESCRIPTION OF PREFERRED EMBODIMENTS

The means providing the features and advantages of the present invention are illustrated in the accompanying drawings wherein:

FIG. 1 is a perspective view of a dental handpiece of a type suitable for incorporation of the handle isolation feature of the present invention;

FIG. 2 is an enlarged side elevational view partly in section of the working or distal end of the dental handpiece of the present invention showing a high-speed gas-driven motor housing and an handle portion adjacent thereto;

FIG. 3 is a perspective view of two disconnected handle members of the dental handpiece of the present invention showing portions of the vibration-inhibiting, substantially-rigid connecting means;

FIG. 4 is a sectional view of a portion of the dental handpiece of FIG. 3 showing assembled one specific embodiment of the vibration-inhibiting, substantially-rigid connecting means;

FIG. 5 is a perspective view of two disconnected handle members of the dental handpiece of this invention showing a portion of a different embodiment of the vibration-inhibiting substantially-rigid connecting means;

FIG. 6 is a sectional view of a portion of the dental handpiece of FIG. 5 showing assembled the vibration-inhibiting, substantially-rigid connecting means of the embodiment of FIG. 5;

FIG. 7 is a perspective view of another embodiment of the dental handpiece of the invention having a substantially-rigid, vibration-inhibiting connection between the handpiece head portion and handle portion; and FIG. 8 is a sectional view of a portion of the dental handpiece showing the assembled vibration-inhibiting, substantially-rigid connection of FIG. 7.

Illustrated in FIG. 1 is a dental handpiece 10 having a handle portion 11 which includes a proximal end 12 and a distal end 13 and having a head portion 14 at handle distal end 13. Contained within head portion 14 is a high-speed gas-driven motor which includes a motor housing 15 having therein a turbine cartridge assembly 16, as shown in FIG. 2. Turbine cartridge assembly 16 includes a rotor shaft 17 journalled on a pair of ball-bearing type roller bearing assemblies 18 disposed on opposite sides of a rotor 19 which is fixedly secured to rotor shaft 17. A plurality of vanes 20 fixedly secured to rotor 19 impart rotation to rotor shaft 17 when a high speed jet of air (or other gas) impinges upon rotor vanes 20, as is well known in the art. A more detailed description of a high speed gas-driven motor that includes a turbine cartridge assembly particularly suitable for the dental handpiece of the invention is found in the aforementioned U.S. application Ser. No. 947,215.

Also illustrated with the dental handpiece of FIGS. 1 and 2 is a shank 21 of a work tool that is clasped by an adjustable collet 22 threadedly engaged within a longitudinal bore 23 of rotor shaft 17. Additional details and advantages of construction of a dental handpiece having the illustrated collet may be found in U.S. Pat. No. 3,120,706 to Turchi et al, the disclosure of which is incorporated herein by reference. A description of means for inserting and removing a work tool, such as a dental burr, into and from collet 22 may be found in U.S. Pat. No. 3,947,966 to Lieb et al.

As shown in FIGS. 1-6 handle portion 11 includes a first member and a second member which are connectable to form a substantially continuous hand-grippable surface extending along elongated handle portion 11 from head portion 14 to proximal end 12 of handpiece 10. The first handle member comprises a neck 24 while the second handle member comprises a barrel 25. It is to be understood that the terms "first handle member" and "second handle member" are arbitrary in the sense that either of neck 24 or barrel 25 could be the first or second handle members.

Neck 24 comprises a generally cylindrical portion 26 which is integrally formed at its forward end with head portion 14, the axis of cylindrical neck portion 26 being substantially perpendicular with the axis of rotor shaft 17 of turbine cartridge assembly 16. Also forming a part of neck 24 is a substantially frusto-conically shaped portion 27, the narrower end of which is integrally formed with an adjacent portion of cylindrical neck portion 26. Cylindrical neck portion 26 and frustro-conical portion 27 provide an outer wall 28 running substantially continuously from head portion 14 to an end wall 29 at the end of neck 24. At least a portion of end wall 29 lies in a plane substantially perpendicular with the axis of frustro-conical portion 27.

The second handle member of handpiece 10 comprises cylindrically shaped barrel 25 which has an outer wall 30 and a forward end wall 31. Barrel 25 is sleeve-like in configuration, that is, barrel 25 has an inner wall 32 which defines a passageway 33 comprising a large portion of the barrel as taken at a cross-section perpendicular to the axis of barrel 25. Thus barrel forward end wall 31, at least a portion of which lies in a plane substantially perpendicular to the axis of barrel 25, has a surface of relatively small cross-sectional area as compared to the total cross-sectional area of passageway 33. Outer wall 30 of barrel 25 and outer wall 28 of neck portion 27 have a plurality of flutes 34, which provide an improved hand-grippable surface, as is known in the art. The first and second handle members are connectable adjacent the junction between end wall 29 of neck 24 and end wall 31 of barrel 25, so that a substantially continuous elongated handle portion for gripping the handpiece is provided by outer walls 28 and 30.

In each of the embodiments of the present invention, as shown in FIGS. 1-6, means for forming a substantially rigid connection is provided between the first and second handle members across the junction between end wall 29 of neck portion 27 and forward end wall 31 when neck 24 and barrel 25 are in proximate abutting relationship. The term "proximate abutting relationship" is intended in this context to indicate that while end wall 29 and end wall 31 are closely adjacent, there remains a gap 35 between end walls 29 and 31.

The means for forming a substantially rigid connection between the first and second handle members can be provided by several different constructions. It is a characteristic of all such constructions that the rigid connecting means forms a connection that is substantially rigid, that is, a user of the dental handpiece while gripping the two-membered handle portion will experience substantially the same tactile control over the handpiece as would be experienced in using a handpiece having an absolutely rigid single-member handle portion. It is also a characteristic of the substantially rigid connecting means that the transfer of vibration between the first and second handle members is substantially inhibited by resilient means interposed between the characteristically non-resilient, metallic elements forming the first and second handle members.

In FIGS. 3 and 4, there is depicted a dental handpiece 10 illustrating one embodiment of the rigid connecting means connecting the first and seond handle members. Neck portion 27, comprising the first handle member, has an elongated boss member in the configuration of a substantially cylindrical shaft 36 projecting in an axial direction from end wall 29. Shaft 36 is integrally formed with frustro-conical portion 27 and thus provides a rigid extension of neck 24. Running cirumferentially about cylindrical shaft side wall 37 is a first groove 38 and a second groove 39 which are in spaced relationship along the axis of shaft 36. Positioned within each of grooves 38 and 39 is a resilient element in the configuration of an annulus provided in this embodiment by a pair of O-rings 40 and 41. Characteristically, O-rings 40 and 41 each has an outer diameter in the radial direction with respect to the axis of shaft 36 which is greater than the outer diameter of shaft 36. The inner diameter of each of O-rings 40 and 41 is approximately the same as, or slightly smaller than, the diameter of shaft 36, as measured at the grooved portions of shaft 36.

Sleeve-like barrel 25, which forms the second handle member of this embodiment, has a cylindrically shaped chamber 42 formed by an opening in forward end wall 31 of barrel 25 which communicates with barrel passageway 33. First handle member shaft 36 and barrel chamber 42 each have a cylindrical configuration complementary to the other so that when neck 24 and barrel 25 are in proximate abutting relationship shaft 36 and chamber 42 are in mating relationship. The diameter of cylindrical shaft 36 is less than the diameter of barrel passageway 33. The difference in these diameters provides an annular-shaped gap 43 between adjacent wall portions of shaft side wall 37 and barrel inner wall 32.

In the assembly of the first and second handle members as depicted in FIG. 4, resilient O-rings 40 and 41 experience compression in the radial direction and thus are expanded or "flattened" in the axial direction with respect to the axis of shaft 36. The resistance of each of O-rings 40 and 41 to radial compression provides a reaction force between shaft 36 and barrel 25 which, in turn, provides resistance to axial displacement of barrel 25 with respect to neck 24. The resistance to compression of O-rings 40 and 41 also opposes the bending of handle portion 11 in a plane containing the respective axes of handle members 24 and 25. In this respect, the degree of bending rigidity is dependent upon the axial spacing between O-rings 40 and 41. Also, the degree of rigidity of the connection is dependent upon the degree of resistance to compression of O-rings 40 and 41 which, in turn, is related to the degree of compression and type of resilient material of which the O-rings are fabricated. In this regard, O-rings 40 and 41 should be fabricated of a resilient material that is sufficiently rigid to provide high resistance to compression, but, at the same time, is a poor transmitter of vibration when in the compressed condition, and which material provides a "high-friction" surface which further restrains movement of shaft 36 and barrel 25 relative to each other. Suitable O-ring materials include, for example, neoprene elastomer, fluorocarbon elastomer, ethylene propylene elastomer and butadiene/acrylonitrile elastomer (known commercially as Buna-N elastomer).

Depicted in FIGS. 5 and 6 is another embodiment of the substantially rigid connecting means of this invention. Upon shaft 36 of neck portion 27 there is a groove 44 running circumferentially about shaft side wall 37. Groove 44 has a dimension in the axial direction slightly less than the entire side wall length of shaft 36. Lying within groove 44 is a resilient element comprising a band 45 of material of cylindrical or annular configuration which has a dimension in the axial direction somewhat less than the length of groove 44. Resilient band 45 has an outer diameter radially outwardly of the axis of shaft 36 greater than the outer diameter of shaft 36 and greater than the inner diameter of barrel passageway 33. The inner diameter of band 45 is approximately the same, or slightly less than, the diameter of shaft 36, as measured at the grooved portion of shaft 36.

In the assembly of the first and second handle members as shown in FIG. 6, resilient band 45 experiences compression in the radial direction and is thus expanded in the axial direction with respect to the axis of shaft 36. The resistance to compression of resilient band 45 provides a substantially rigid connection between neck 24 and barrel 25 much the same as described above for the substantially rigid connecting means of FIGS. 3 and 4. Suitable materials for fabricating resilient band 45 are as described above for O-rings 40 and 41.

As mentioned, the resistance to compression provided by O-rings 40 and 41 or cylindrical band 45 of the embodiments of FIGS. 3–6, whereby the O-rings or band are forced into contact with inner wall 32, prevents or retards axial movement of the first and second handle members relative to each other during routine or ordinary use of the handpiece. There may be provided, however, stop means for preventing or retarding axial movement of one of the handle members, such as neck 24, relative to the other handle member, such as barrel 25, in addition to, or in place of, the resistance to compression force provided by the contact of the resilient material with inner wall 32 of barrel 25. Thus shaft 36 can have a recess 46 oriented radially outwardly of, and transverse to, the axis of shaft 36. Recess 46 terminates in the body of shaft 36 and is in communication with gap 43. In the embodiment of FIGS. 3 and 4, recess 46 lies between O-rings 40 and 41, while in the embodiment of FIGS. 5 and 6, the recess communicates with groove 44 through hole 47 within band 45. An opening or port 48 in outer wall 30 of barrel 25 is aligned with recess 46 as depicted in FIGS. 3 and 4 and, in the embodiment of FIGS. 5 and 6, with hole 47 in band 45, when the first and second handle members are in proximate abutting relationship. A stop pin 49 lies within and forms a sleeve or friction fit with recess 46 in shaft 36, and extends radially outwardly from shaft 36 into opening 48 of barrel 25. Opening 48 has an inner diameter only slighly greater than the outer diameter of stop pin 49. Hence, with stop pin 49 lying coaxially within opening 48, there exists a slight gap 50 between stop pin 49 and the adjacent wall of opening 48. It is preferred that stop pin 49 have a cross-sectional area less than about 15 percent of the cross-sectional area of shaft 36, in order to minimize the amount of mass available for transmitting vibration through stop pin 49 in the event stop pin 49 is in simultaneous contact with both handle members as, for example, when bending forces are applied to handle portion 11.

It should be apparent that, in addition to preventing or retarding axial movement, the described stop means also prevents or retards rotational movement of the first and second handle members relative to each other about the longitudinal axis of handle portion 11 due to the limited size of opening 48.

Prevention of rotation of the first and second handle members relative to each other may be accomplished by other means than the described stop means. For example, neck 24 may have an elongated boss member projecting from end wall 29 of neck portion 27 which is non-circular in a cross-section taken transverse to the axis of the elongated boss member. Thus the boss member may be oval or polygonal in cross-section. A complementary shaped chamber within end wall 31 of barrel 25, when in mating relationship with the boss member, would form a handle portion having handle members that are non-rotatable about the longitudinal axis of the handle portion.

It is a feature of the means for preventing or retarding axial or rotational movement that in the normally assembled embodiments of FIGS. 3–6, there is substantially no metal-to-metal contact between neck 24 and barrel 25. The provision of gap 50 within the means for retarding axial movement preserves the integrity of the vibration-transfer inhibiting feature of the substantially rigid connecting means of this invention.

It should be mentioned that gap 50 could be established as well between recess 46 and stop pin 49, in which case stop pin 49 would be fixedly secured within opening 48 in barrel 25. Also, with regard to the embodiment of FIGS. 5 and 6, stop pin 49 could be retained in place by a friction fit with hole 47 of resilient band 45. In the latter embodiment, gap 50 can be provided between stop pin 49 and the walls of either, or both, recess 46 and opening 48.

There may be included within the scope of the means for retarding or preventing axial or rotational movement of the connectable portions of the handpiece of the invention constructions other than the illustrated stop pin-and-recess or opening arrangement. For example, in place of stop pin 49 there may be a screw threadably engaged in one or the other of the connectable portions. The screw may engage, or be in contact with, both of the connectable portions, although it is preferred there by a gap between the screw and one of the handpiece connectable portions. Where the screw is in contact with both handpiece connectable portions, it is preferred that there be a resilient material, such as one of the aforementioned resilient materials for forming O-rings 40 and 41, covering the threaded portion of the screw that engages a threaded portion of one of the handpiece connectable portions. It should also be mentioned that stop pin 49 could be fabricated entirely of one of the aforementioned resilient materials. Or, the entire axial or rotational movement preventing means could be molded integrally with the resilient means forming, for example, the band 45 of resilient material.

As mentioned, it is a feature of a dental handpiece of the invention that there be substantially no metal-to-metal contact between the first and second handle members of the handle portion, there being resilient, vibration-transfer inhibiting means interposed between the closely adjacent metallic portions of the substantially rigid connecting means. Because a resilient material by nature will deflect when a sufficient force is applied to it, there is required within the substantially rigid connecting means of the invention stop means to limit the movement of the first and second handle members due to deflection forces created in use of the handpiece. It has been found that annular gap 35 that exists between end wall 29 of neck portion 27 and end wall 31 of barrel 25 should have a dimension in the axial direction in the range of about 0.002 inch to about 0.015 inch, and preferably in the range of about 0.007 inch to 0.010 inch.

A dental handpiece having a two-membered handle portion which includes the substantially rigid connecting means of this invention may be used advantageously in combination with other commercially available handpiece features. For example, there may be included within handle portion 11 of dental handpiece 10 means for conveying water or air, or both, to head portion 14. Neck 24 has a central passageway 51 in communication with passageway 33 of barrel 25. Extending through passageways 33 and 51 is a tube 52 for conveying a stream of gas, such as air, from a source thereof (not shown), to an inlet port 53 in motor housing 15, as shown in FIG. 2. Also contained within passageways 33 and 51 is a pair of tubes for conveying air and water separately, to spray-forming means 54 comprised of a pair of discharge ports located at the termini of the air and water tubes adjacent work tool shank 21. The water spray provided by spray-forming means 54 is useful, for example, for cooling a dental bur during a drilling operation. Other suitable spray-forming means, together with details of construction, may be found in U.S. Pat. No. 3,525,154 to N. H. Lieb.

Light guiding means, such as a fiber-optics bundle 55, may also extend through passageways 33 and 51. The fiber-optics bundle 55 has a terminus 56 which directs light in the vicinity of the work tool during use of the handpiece. Details of construction of a suitable light guiding means for inclusion in the handpiece of the invention may be found in U.S. Pat. No. 4,020,556 to K. Sotman.

Although the various substantially rigid connecting means have been illustrated as connecting neck and barrel portions of a dental handpiece handle portion, the substantially rigid connecting means could be utilized between other portions of the handpiece as well. For example, a substantially rigid connection with resilient means of the type described herein could be used between motor housing 15 and a separately connectable portion of neck 24. Or, the described connection could be utilized between cylindrical portion 26 and frustro-conical portion 27 of neck 24. Or, a plurality of rigid connections having resilient means could be incorporated between several separately connectable abutting portions of a handpiece. In FIGS. 7 and 8, there is illustrated in detail an embodiment of the handpiece of the invention wherein the substantially rigid connection is between connectable portions of the handpiece other than the handle members. There is integrally formed with head portion 14, as shown in FIG. 7, a cylindrical shaft 36 having first and second grooves 38 and 39, respectively, running circumferentially about shaft side wall 37, as similarly depicted for the connection means of FIGS. 3 and 4. A pair of O-rings 40 and 41, lying in a compressed condition within grooves 38 and 39, respectively, provide support for a portion of inner wall 60 of cylindrical neck section 26, and provide resistance to axial movmement and bending movements of neck portion 26 with respect to head portion 14, in a manner as described in detail above. As shown in FIG. 8, a gap 61 is provided between outer wall 62 of head portion 14 and an end wall 63 at the distal end of handle portion 11. Gap 61 has dimensions in the aforementioned preferred ranges as given for the embodiments of FIGS. 1–6. A recess 46 in the body of shaft 36 contains a driven stop pin 49. Stop pin 49 extends across a gap 64 formed between shaft side wall 37 and neck inner wall 60 into an opening 48 which passes between inner wall 60 and outer wall 28. Stop pin 49 has a diameter less than the diameter of opening 48 such that a gap 50 exists between a portion of stop pin 49 and the wall of opening 48, as described above for the embodiments of FIGS. 3–6.

While this invention has been described with reference to specific embodiments thereof, it should be understood by those skilled in this art that various changes may be made and equivalents may be substituted without departing from the true spirit and scope of the invention. All such modifications are intended to be within the scope of the claims appended hereto.

What is claimed is:

1. A dental handpiece comprising:
 a handle portion having a proximal end and a distal end;
 a housing for a gas driven motor connected to said handle portion at said distal end;
 said handle portion including a first handle member having an outer wall and an end wall and a second handle member having an outer wall and an end wall, said first and second handle members connectable to each other at a junction so as to form a substantially continuous elongated handle portion with said outer walls providing a surface for gripping said handpiece;
 means for forming a substantially rigid connection between said first handle member and said second handle member adjacent the junction, when said first and second handle member end walls are in proximate abutting relationship;
 said means for forming the substantially rigid connection including resilient means interposed between said first and said second handle members such that said first and second handle members are not in direct contact with each other, said resilient means substantially inhibiting the transfer of vibration between said first and second handle members.

2. The dental handpiece of claim 1 wherein said means for forming the rigid connection between said first handle member and said second handle member comprises:

an elongated boss member projecting from one of said first and said second handle member end walls, said boss member having at least one side wall;

the other of said first and said second handle members having a chamber in said end wall thereof, said chamber defined by at least one inner side wall of said other handle member;

said elongated boss member and said chamber each having a configuration complementary to the other so as to form a mating relationship when said handle member end walls are in proximate abutting relationship;

said elongated boss member having a diameter less than the diameter of said chamber taken in a plane generally transverse to the axis of said elongated boss member, there being formed a gap between adjacent portions of said side wall of said elongated boss member and said inner side wall of said chamber when said elongated boss member and said chamber are in mating relationship;

wherein said resilient means is interposed in a compressed condition in the gap between adjacent portions of said side walls.

3. The dental handpiece of claim 2 wherein said elongated boss member is a cylindrically shaped shaft projecting from one of said first and said second handle member end walls, said chamber is cylindrically shaped having longitudinal and radial dimensions greater than those of said cylindrically shaped shaft, and said resilient means circumferentially overlies said shaft.

4. The dental handpiece of claim 3 wherein said resilient means comprises at least two O-rings fabricated of resilient material, said O-rings being in spaced relationship along the axis of said shaft.

5. The dental handpiece of claim 3 wherein said resilient means is a continuous band of resilient material overlying substantially the entire side wall of said shaft.

6. The dental handpiece of claim 3 further including stop means for retarding axial or rotational movement of one of said first and second handle members relative to the other of said first and second handle members.

7. The dental handpiece of claim 6 wherein said stop means for retarding axial or rotational movement comprises:

a recess in the side wall of said shaft, an opening in said handle member having said defined chamber, said opening in communication with said outer and inner walls of said chamber, said opening being in alignment with said recess when said handle members are positioned in abutting and mating relationship; and a stop pin within said recess and said opening, said stop pin being in contact with with said shaft or with said handle member having said chamber, but not both, said pin retarding axial and rotational movement of said shaft within said chamber.

8. The dental handpiece of claim 7 wherein said stop pin has a cross-sectional area less than about 15 percent of the cross-sectional area of said shaft.

9. The dental handpiece of claim 1 wherein said resilient means is fabricated of a resilient material selected from the group consisting of neoprene elastomer, fluorocarbon elastomer, ethylene propylene elastomer and butadiene/acrylonitrile elastomer.

10. A dental handpiece comprising:

a handle portion having a proximal end and a distal end, said handle portion having a head portion including a housing for a gas-driven motor, said head portion connected to said handle portion at said distal end;

said handle portion distal end having an end wall and said head portion having an outer wall adjacent said end wall of said handle portion distal end;

means for forming a substantially rigid connection between said handle portion end wall and said head portion outer wall, when said handle portion and said head portion are in proximate abutting relationship;

said means for forming the substantially rigid connection including resilient means interposed between said handle portion and said head portion such that said handle portion and said head portion are not in direct contact with each other, said resilient means substantially inhibiting the transfer of vibration between said head portion and said handle portion.

11. The dental handpiece of claim 10 wherein said means for forming the substantially rigid connection between said handle portion and said handle portion comprises:

an elongated boss member projecting from either of said handle portion end wall or said head portion outer wall, said boss member having at least one side wall;

the other of said handle portion end wall or said head portion outer wall having a chamber therein, said chamber defined by at least one inner side wall of said other handle portion or said head portion;

said elongated boss member and said chamber each having a configuration complementary to the other so as to form a mating relationship when said handle portion end wall and said head portion outer wall are in proximate abutting relationship;

said elongated boss member having a diameter less than the diameter of said chamber taken in a plane generally transverse to the axis of said elongated boss member, there being formed a gap between adjacent portions of said side wall of said elongated boss member and said inner side wall of said chamber when said elongated boss member and said chamber are in mating relationship;

wherein said resilient means is interposed in a compressed condition in the gap between adjacent portions of said side walls.

12. The dental handpiece of claim 11 wherein said elongated boss member is a cylindrically shaped shaft, said chamber is cylindrically shaped having longitudinal and radial dimensions greater than those of said cylindrically shaped shaft, and said resilient means circumferentially overlies said shaft.

13. The dental handpiece of claim 12 wherein said resilient means comprises at least two O-rings fabricated of resilient material, said O-rings being in spaced relationship along the axis of said shaft.

14. The dental handpiece of claim 12 wherein said resilient means is a continuous band of resilient material overlying substantially the entire side wall of said shaft.

15. The dental handpiece of claim 12 further including stop means for retarding axial or rotational movement of said handle portion relative to said head portion.

16. The dental handpiece of claim 15 wherein said stop means for retarding axial or rotational movement comprises:
 a recess in said side wall of said shaft;
 an opening in said chamber side wall, said opening being in alignment with said recess when said head portion outer wall and said handle portion end wall are positioned in abutting and mating relationship; and
 a stop pin within said recess and said opening,
 said stop pin being in contact with said shaft or said handle portion, but not both, said stop pin retarding axial or rotational movement of said shaft within said chamber.

17. The dental handpiece of claim 16 wherein said stop pin has a cross-sectional area less than about 15 percent of the cross-sectional area of said shaft.

18. The dental handpiece of claim 10 wherein said resilient means is fabricated of a resilient material selected from the group consisting of neoprene elastomer, fluorocarbon elastomer, ethylene propylene elastomer and butadiene/acrylonitrile elastomer.

* * * * *